US010568656B2

(12) United States Patent
Saitoh et al.

(10) Patent No.: US 10,568,656 B2
(45) Date of Patent: Feb. 25, 2020

(54) MEDICAL KNIFE

(71) Applicant: MANI, Inc., Utsunomiya-shi, Tochigi (JP)

(72) Inventors: Takatomo Saitoh, Utsunomiya (JP); Masato Suda, Utsunomiya (JP)

(73) Assignee: MANI, INC., Tochigi (JP)

( * ) Notice: Subject to any disclaimer, the term of this patent is extended or adjusted under 35 U.S.C. 154(b) by 0 days.

(21) Appl. No.: 15/121,612

(22) PCT Filed: Feb. 12, 2015

(86) PCT No.: PCT/JP2015/053758
§ 371 (c)(1),
(2) Date: Aug. 25, 2016

(87) PCT Pub. No.: WO2015/129461
PCT Pub. Date: Sep. 3, 2015

(65) Prior Publication Data
US 2016/0361081 A1 Dec. 15, 2016
US 2018/0333167 A2 Nov. 22, 2018

(30) Foreign Application Priority Data

Feb. 28, 2014 (JP) .................................. 2014-039056

(51) Int. Cl.
*A61B 17/3211* (2006.01)
*A61B 17/00* (2006.01)
*A61B 90/00* (2016.01)

(52) U.S. Cl.
CPC . *A61B 17/3211* (2013.01); *A61B 2017/00424* (2013.01); *A61B 2017/00778* (2013.01); *A61B 2090/0801* (2016.02)

(58) Field of Classification Search
CPC ........ A61B 2090/08; A61B 2090/0801; A61B 17/3211; A61B 2017/00424;
(Continued)

(56) References Cited

U.S. PATENT DOCUMENTS 438,734 A * 10/1890 Klopp ..................... B26B 11/00
30/155
455,610 A * 7/1891 Davis ..................... B26B 11/00
30/152
(Continued)

FOREIGN PATENT DOCUMENTS

DE 19707083 A1 * 10/1997 ............. B26B 29/02
JP 3053471 U 10/1998
(Continued)

OTHER PUBLICATIONS

International Search Report for Application No. PCT/JP2015/053758 dated Mar. 24, 2015.

*Primary Examiner* — Jason Daniel Prone
(74) *Attorney, Agent, or Firm* — Isshiki International Law Office; Joseph P. Farrar, Esq.

(57) ABSTRACT

A medical knife configured such that a cutting blade does not face upward when placed on a stand. A medical knife (10) includes a handle (20) and a cutting portion (30). The handle (20) includes a protrusion (20*a*) that makes point contact with a flat surface or makes line contact with the flat surface along the axis of the handle when trying to place the medical knife on the flat surface with a cutting blade (30*a*) of the cutting portion (30) of the medical knife facing upward. Moreover, the protrusion (20*a*) makes contact with a horizontal surface at a position deviating from a position defined by a line extending downward vertically from the center of gravity of the medical knife (10).

2 Claims, 2 Drawing Sheets

(58) Field of Classification Search
CPC ... A61B 2017/00455; B26B 1/10; B26B 3/00; B26B 11/00
USPC .................. 30/153, 155–162, 340, 342–344; 606/167; D24/147; D22/118; D8/99
See application file for complete search history.

(56) References Cited

U.S. PATENT DOCUMENTS

| | | | | |
|---|---|---|---|---|
| 1,728,619 | A * | 9/1929 | Lambert | B26B 3/00 30/343 |
| 1,822,828 | A * | 9/1931 | Stueckman | B26B 9/00 30/144 |
| 2,045,192 | A * | 6/1936 | Kuhar | B26B 3/00 30/298.4 |
| D152,727 | S * | 2/1949 | Peterson | 30/355 |
| 2,685,734 | A * | 8/1954 | Klein | A22B 5/0047 30/344 |
| 3,064,352 | A | 11/1962 | Koe | |
| 3,601,893 | A * | 8/1971 | Knox | B26D 3/065 30/340 |
| D224,388 | S * | 7/1972 | Wood | D8/99 |
| 3,747,211 | A * | 7/1973 | Calabrese | B26B 1/02 30/155 |
| 4,071,952 | A * | 2/1978 | Meshulam | B26B 29/025 30/151 |
| D270,655 | S * | 9/1983 | Collins | D8/99 |
| 4,442,559 | A * | 4/1984 | Collins | B26B 3/06 7/158 |
| 4,535,987 | A * | 8/1985 | Dikoff | A63B 57/00 7/138 |
| 4,688,287 | A * | 8/1987 | Siino | B26B 11/00 7/118 |
| D361,254 | S * | 8/1995 | Silberstein | D8/99 |
| 5,584,123 | A * | 12/1996 | Chi | B26B 11/00 30/162 |
| D386,059 | S * | 11/1997 | O'Hara | D8/99 |
| D386,960 | S * | 12/1997 | O'Hara | D8/99 |
| D397,016 | S * | 8/1998 | Pohl | D8/99 |
| D403,942 | S * | 1/1999 | Gullette | D8/99 |
| D407,002 | S * | 3/1999 | Morton | D8/99 |
| D420,883 | S * | 2/2000 | Zaha | D8/99 |
| 6,029,357 | A * | 2/2000 | Morton | B26B 1/10 30/340 |
| D422,669 | S * | 4/2000 | Elishewitz | D22/118 |
| 6,082,232 | A * | 7/2000 | Anderson | B25F 1/003 7/118 |
| 6,591,505 | B2 * | 7/2003 | Flavigny | B26B 1/042 30/161 |
| D488,697 | S * | 4/2004 | Rae | D8/99 |
| D496,425 | S * | 9/2004 | Carter, III | D22/118 |
| D497,531 | S * | 10/2004 | Carter, III | D8/99 |
| 6,884,240 | B1 * | 4/2005 | Dykes | A61B 17/3211 30/162 |
| 6,948,250 | B1 * | 9/2005 | Caiafa, Jr. | B26B 1/08 30/162 |
| D553,468 | S * | 10/2007 | Freeman | D8/99 |
| 7,306,615 | B2 * | 12/2007 | Wilson | A61B 17/3211 30/151 |
| D610,646 | S * | 2/2010 | Harsey, Jr. | D22/118 |
| D639,632 | S * | 6/2011 | Freeman | D8/99 |
| 8,117,755 | B2 * | 2/2012 | Scimone | B26B 3/08 30/151 |
| D657,435 | S * | 4/2012 | Wilke | D22/118 |
| D670,149 | S * | 11/2012 | Yang-Fu | D8/99 |
| D679,975 | S * | 4/2013 | Pelton | D22/118 |
| 8,409,231 | B2 | 4/2013 | Dunn | |
| 8,695,138 | B2 * | 4/2014 | Pelton | B26B 11/006 30/161 |
| 8,707,490 | B1 * | 4/2014 | Pelton | B26B 1/00 7/158 |
| D706,605 | S * | 6/2014 | Cheng | D8/99 |
| 8,875,405 | B2 * | 11/2014 | Trees | A61B 17/3211 606/167 |
| 9,038,223 | B2 * | 5/2015 | Carson | B26B 9/00 7/118 |
| D734,117 | S * | 7/2015 | Cheng | D8/99 |
| D738,181 | S * | 9/2015 | Kanaan | D8/99 |
| 2001/0039738 | A1 * | 11/2001 | Bachta | B23D 49/11 30/340 |
| 2003/0005587 | A1 * | 1/2003 | Alfi | B26B 3/00 30/340 |
| 2005/0101978 | A1 | 5/2005 | Ziemer | |
| 2006/0080840 | A1 * | 4/2006 | Freeman | B26B 3/06 30/151 |
| 2006/0218800 | A1 * | 10/2006 | Stevens | B26B 3/00 30/314 |
| 2008/0222895 | A1 * | 9/2008 | Marfione | A62B 3/00 30/151 |
| 2010/0263218 | A1 * | 10/2010 | Bookhamer | B26B 3/02 30/342 |
| 2011/0010868 | A1 * | 1/2011 | Palladino | B26B 5/00 7/158 |
| 2011/0098734 | A1 * | 4/2011 | Cote | A61B 17/3211 606/167 |
| 2012/0017443 | A1 * | 1/2012 | Hao | B26B 1/046 30/161 |

FOREIGN PATENT DOCUMENTS

| | | | | |
|---|---|---|---|---|
| JP | | 2004147914 A | 5/2004 | |
| JP | | 2011110198 A | 6/2011 | |
| JP | WO | 2015129461 A1 * | 9/2015 | ......... A61B 17/3211 |

* cited by examiner (a)  (b)

MEDICAL KNIFE

CROSS-REFERENCE TO RELATED APPLICATION

This application is a national phase entry under 35 U.S.C. § 371 of International Application No. PCT/JP2015/053758, filed on Feb. 12, 2015, which claims priority to Japanese Patent Application No. 2014-039056, filed on Feb. 28, 2014, the disclosures of which are incorporated herein by reference.

TECHNICAL FIELD

The present invention relates to a medical knife, in particular to a medical knife used for making an incision in a coronary artery during heart surgery.

BACKGROUND ART

When stricture or obstruction (thrombus) of a coronary artery of the heart occurs, bypass vascular transplantation surgery for bridging over the stricture or obstruction is conducted. This surgery makes an incision in a junctional part of a blood vessel using a medical knife, cuts with scissors along this incision to enlarge it to a desired size, and sutures and connects an end of a blood vessel for transplantation to the enlarged part.

The medical knife used in this case may be the medical knife described in Patent Document 1, for example. FIG. 5 is a diagram illustrating a conventional medical knife described in Patent Document 1. This medical knife 51 includes a cutting portion 53 accompanied in a knife holder 54, and is used with the knife holder 54 attached to an attaching part 52a that extends from a metal handle 52.

Here, there are two types of the attaching part 52a: one that is at an angle with the handle 52, and the other that is at no angle with the same. Moreover, according to the shape of the knife holder 54, there are two types of the cutting portion 53: one that is at an angle with the attaching part 52a, and the other that is at no angle with the same. Note that the attaching part 52a of the medical knife illustrated in FIG. 5 is at no angle with the handle 52 and the cutting portion 53 is at an angle with the attaching part 52a.

The medical knife 51 having such a configuration can have diverse angles of the cutting portion 53 with the handle 52 in accordance with a combination of the attaching part 52a having or not having an angle and the knife holder 54 having or not having an angle, and can therefore be used for different purposes according to the position of the diseased part or preference of the surgeon.

In a large-scale operation such as heart surgery, several kinds of the medical knife 51 and other tools etc. are used in this manner. When replacing the medical knife 51 or changing it to another tool, etc., the medical knife 51 in hand is once placed on a stand. In this case, the medical knife 51 illustrated in FIG. 5 is used with a cutting blade facing upward when making an incision. As a result, when laying this medical knife 51 on the stand, it is generally placed with the cutting blade facing upward. However, if the cutting blade of the medical knife 51 placed on the stand is facing upward, there is a risk of injury by the cutting blade of the medical knife 51 when the surgeon places his/her hand on the stand or when holding another knife or tool, etc. in his/her hand.

Moreover, since the cutting portion 53 of the medical knife 51 used to form an incision in a coronary artery often has an angle with the handle 52, the medical knife 51 may roll when placing it on the stand, thereby possibly making the cutting blade of the cutting portion 53 touch the stand, and damaging the cutting blade at that time.

PRIOR ART DOCUMENTS

Patent Documents

[Patent Document 1] JP 2004-147914 A

DISCLOSURE OF THE INVENTION

Problem to be Solved by the Invention

In light of these conditions, the present invention aims to provide a medical knife having a configuration such that the cutting blade does not face upward when laid on a stand. It also aims to prevent the cutting blade from touching the stand even if the medical knife turns over onto one side.

Solution to the Problem

A medical knife of the present invention is characterized by including a handle and a cutting portion. The handle includes a protrusion that makes point contact with a flat surface at a point or makes line contact with the flat surface along the axis of the handle when trying to place the medical knife on the flat surface with a cutting blade of the cutting portion of the medical knife facing upward.

When trying to place the medical knife on a horizontal surface with the cutting blade facing upward, the protrusion should make contact with the horizontal surface at a position deviating from a position defined by a line extending downward vertically from the center of gravity of the medical knife. The handle should further include a stabilizing part that makes contact with the horizontal surface at multiple places or a surface to make the medical knife stand still on the horizontal surface while the cutting blade is facing in the horizontal direction or in a lower direction than the horizontal direction, and while the cutting blade is not making contact with the horizontal surface.

Advantageous Effect of the Invention

According to the medical knife of the present invention, even when trying to place the cutting blade facing upward, this brings about a beneficial effect that due to contact of the protrusion that is provided to the handle with the flat surface, the medical knife turns over onto one side and the cutting blade does not face upward.

Moreover, since even if the medical knife turns over onto one side, it stands still while the cutting blade is facing in the horizontal direction or in a lower direction than the horizontal direction, and while the cutting blade is not making contact with the horizontal surface, this also brings about a beneficial effect of the cutting blade thereby not becoming damaged by making contact with the horizontal surface.

DESCRIPTION OF EMBODIMENTS

An embodiment of the present invention is described while referencing the attached drawings.

Figure 1:
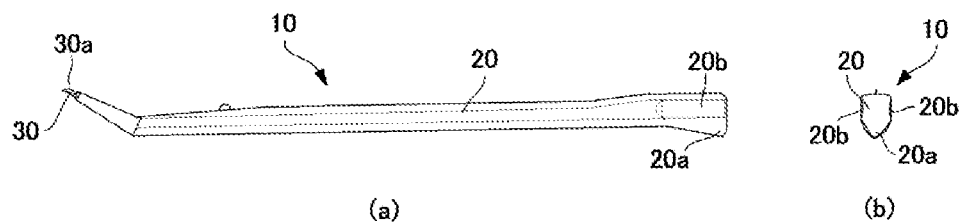
FIG. 1 is a diagram illustrating a medical knife of the present invention, wherein (a) is viewed from a side and (b) is viewed from the end of a handle.

FIG. 1 is a diagram illustrating a medical knife of the present invention; wherein (a) is viewed from a side and (b) is viewed from the end of a handle. This medical knife 10 is made up of a cutting portion 30 and a handle 20. The handle 20 is made of resin basically, but there is not a problem even if made of metal. There are two types of knives: one that has the cutting portion 30 at an angle with the axis of the handle 20, as in (a), and the other that has the cutting portion 30 straight along the axis. Moreover, there are various angle sizes.

Since this medical knife 10 is used with a cutting blade 30a of the cutting portion 30 facing upward, the cutting portion 30 is often facing upward when a surgeon places the medical knife 10 on a horizontal surface (on a horizontal surface or a flat surface with a slight slope) such as a stand or the like, as shown in FIG. 1. If the knife remains still on the horizontal surface such as a stand with the cutting blade 30a facing upward, the risk of injuring the surgeon increases, as mentioned before.

Therefore, the medical knife 10 according to the present invention has the handle 20 with a protrusion 20a. The protrusion 20a should be provided at a position not interfering with when the medical knife 10 is used, more specifically at the end of the handle 20. The shape of the protrusion 20a is a pointed protrusion so that when the medical knife 10 is laid down with the cutting blade 30a facing upward, it makes point contact with the horizontal surface such as a stand etc. or makes line contact along the axis of the handle 20. In other words, the protrusion 20a is a portion protruding in a direction opposite to the cutting blade 30a, and has a shape that looks as if the protrusion apex is making contact with the horizontal surface when viewed from the end of the handle 20. When the apex of such a protrusion 20a makes contact with the horizontal surface, the medical knife 10 loses its balance and turns over onto one side since the contact part is not a flat surface. That is, the medical knife 10 has a configuration such that it cannot be laid down with the cutting blade 30a facing upward.

Figure 2:
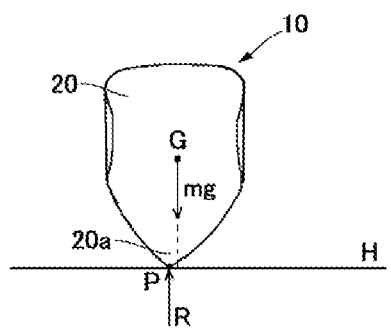
FIG. 2 represents an upright state of the surgical knife.

When such a protrusion 20a is provided, while the medical knife 10 basically turns over onto one side, the knife is sometimes hard to turn over onto one side if it is placed on gauze etc. that is laid on the stand. A medical knife 10 that is devised to turn over onto one side easily is illustrated in FIG. 2. FIG. 2 is a diagram describing a mechanism of a protrusion that makes it easier to turn the medical knife over onto one side. The shape of the end surface of the handle 20 to which the protrusion 20a shown in this drawing is provided is approximately a pentagon like a baseball home plate, where the position of the sharp edge is the protrusion 20a.

Here, the end shape of the handle 20 is not symmetrical. Namely, when trying to lay the knife on a horizontal surface H with the cutting blade 30a facing upward, contact point P of the protrusion 20a and the horizontal surface H should deviate from a position defined by a line extending downward vertically from the center of gravity G of the medical knife 10. As a result, since the direction of action of the self-weight mg of the medical knife 10 and direction of action of the reaction force R from the horizontal surface H are not on the same line, a force couple works on the medical knife 10 and rotates it. That is, displacing the apex position of the protrusion 20a results in a configuration of the medical knife 10 that can be easily turned over onto one side. More specifically, the knife turns over clockwise onto one side in FIG. 2.

Figure 3:
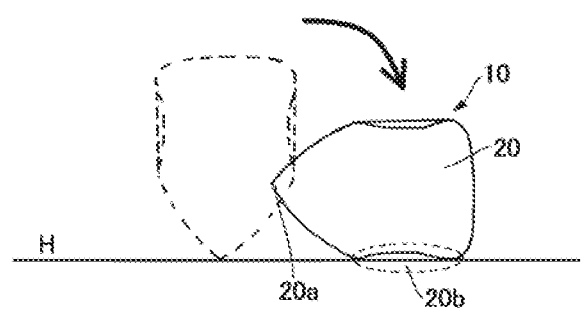
FIG. 3 represents an overturned state of the surgical knife, overturned from the state illustrated in FIG. 2.

FIG. 3 is a diagram illustrating a handle end of the medical knife turned over onto one side. When the medical knife 10 turns over onto one side, the apex of the protrusion 20a separates from the horizontal surface H, and the cutting blade 30a faces nearly in the horizontal direction. At this time, a side of the end of the handle 20 makes contact with the horizontal surface H; however, if the shape of the end of the handle 20 is an approximate pentagon as shown in FIG. 3, the end of the handle 20 makes contact at a surface with the horizontal surface H, and thus does not turn any further and is stable.

Here, when the cutting blade 30a is standing still and facing nearly in the horizontal direction, a part making contact with the horizontal surface H is a stabilizing part 20b. The stabilizing part 20b is provided in a direction intersecting the direction in which the cutting blade 30a faces. Facing nearly in the horizontal direction means that the cutting blade 30a is facing in the horizontal direction or in a lower direction than the horizontal direction, and also that the cutting blade 30a is not making contact with the horizontal surface H. The stabilizing part 20b is formed to make contact at a surface like FIG. 3 with the horizontal surface H or to make contact at a plurality of points with the horizontal surface H. Note that having a plurality of contact points means, for example, the case of a combination of a line contact and a point contact, the case of three or more point contacts, etc. Moreover, the prepared positions of the stabilizing part 20b should be, as with the protrusion 20a, positions not interfering with when the medical knife 10 is used, more specifically the end of the handle 20. That is, it is preferable to form the protrusion 20a and the stabilizing part 20b as a unified body.

Furthermore, if the stabilizing part 20b makes contact at a surface with the horizontal surface H or contact at a plurality of points therewith, it is more difficult for such a state to occur as the medical knife 10 turns so much when turning over onto one side that the cutting blade 30a faces downward and thereby making contact with the horizontal surface H. That is, even when the cutting portion 30 has an angle with the handle 20, the cutting blade 30a can be prevented from making contact with the horizontal surface H such as a stand or the like, and thus there is no worry of chipping the cutting blade 30a.

Note that when forming the handle 20 from resin, in order to secure bending rigidity during use, the cross-section of the handle 20 is often made to be a vertically long ellipse, rectangle, etc. along the length of the cutting blade 30a (up and down in FIG. 2). As a result, the part in contact with the horizontal surface H can be made large when forming the stabilizing part 20b, thereby increasing stability when it is standing still.

Figure 4:
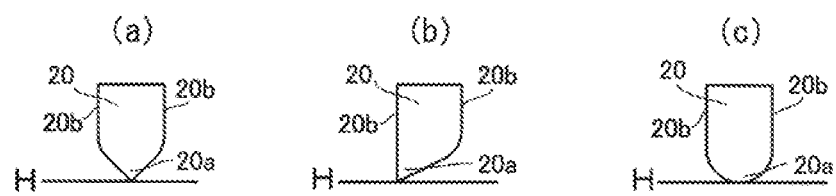
FIG. 4 is a diagram illustrating an embodiment of the handle end of the medical knife.
Figure 5:
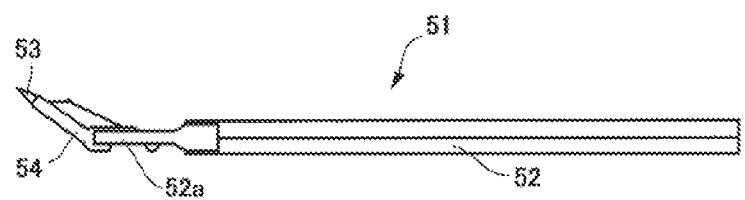
FIG. 5 is a diagram illustrating a conventional medical knife.

FIG. 4 is a diagram illustrating an embodiment of the handle end of the medical knife, wherein (a) shows a baseball home plate shape, (b) shows a laterally-disposed trapezoid, and (c) shows a round apex of the protrusion. These are merely examples, and other shapes are also possible. Note that such shapes as exemplified here allow formation of the protrusion 20a and the stabilizing part 20b of the medical knife 10 as a unified body.

In the case of the home plate shape of (a), the acute angle portion is the protrusion 20a, and the left and right sides are the stabilizing parts 20b. Therefore, since it is unstable when the protrusion 20a makes contact with the horizontal surface H, the medical knife 10 turns over onto one side and stabilizes when the stabilizing part 20b makes contact with the horizontal surface H. Moreover, as mentioned before, if the protrusion 20a is shifted to either the left or the right, it becomes easier for the medical knife 10 to turn over onto one side.

The case of the laterally-disposed trapezoid of (b) results from shifting the protrusion 20a of (a) to the left side. This case turns over onto one side to the right in the drawing and stabilizes. Note that the stabilizing part 20b on the left side may be placed making contact with the horizontal surface from the beginning.

The case of the round apex of the protrusion 20a of (c) results from rounding the acute angle portion of (a), and as in (a), the left and right sides are the stabilizing parts 20b. Since it makes point-contact with the horizontal surface H or makes line-contact with it along the axis of the handle, the cutting blade 30a cannot be placed facing upward, as with the home plate shape of (a). Note that if the apex of the protrusion 20a is round, there is an advantage that when the medical knife 10 turns over onto one side, the contact position with the horizontal surface H is smoothly shifted from the protrusion 20a to the stabilizing point 20b, thereby making it easy for the medical knife 10 to stand still.

The above embodiment has been explained using the medical knife utilized in heart surgery. However, since use of a medical knife other than for heart surgery is of course also dangerous when placed with the cutting blade facing upward, the same configuration according to the present invention may be further applied to other medical knives.

In addition, provision of such a protrusion and stabilizing part protects the safety of the surgeon, and attention no longer needs to be given to what direction the medical knife is placed down during surgery.

LIST OF REFERENCES

10: Medical Knife
20: Handle
20a: Protrusion
20b: Stabilizing part
30: Cutting portion
30a: Cutting blade
P: Point of contact
G: Center of gravity
H: Horizontal surface

The invention claimed is:
1. A surgical knife, in an upright state comprising:
a handle
including an end surface comprising a protrusion having a vertical taper defining a point; and
a cutting portion comprising a cutting blade having an upward facing cutting edge, attached to another end of the handle opposite the end surface with the protrusion, the point of the protrusion protruding in an opposite direction than the cutting edge,
wherein the point of the protrusion is at a position offset laterally from a latitudinal center of gravity of the surgical knife, such that the point of the protrusion is configured to make point contact with a horizontal flat surface at a position deviating laterally from the latitudinal center of gravity of the surgical knife,
wherein a longitudinal axis of the handle rises in a straight line from the cutting portion through the end surface.
2. The surgical knife of claim 1, wherein the handle further comprises a stabilizing part that makes contact with the horizontal flat surface at multiple points or on a plane defined by a surface of the stabilizing part that contacts the horizontal flat surface to make the surgical knife rest on the horizontal flat surface in an overturned state in which the cutting blade lies in a plane parallel to the longitudinal axis of the handle and below a horizontal plane defined by an upper surface of the handle without the cutting blade contacting the horizontal flat surface.

* * * * *